United States Patent [19]

Hussein

[11] 4,112,066
[45] Sep. 5, 1978

[54] BREATH FRESHENER COMPOSITION AND METHOD

[75] Inventor: Ma'moun M. Hussein, Rye, N.Y.

[73] Assignee: Life Savers, Inc., New York, N.Y.

[21] Appl. No.: 697,887

[22] Filed: Jun. 21, 1976

[51] Int. Cl.$^2$ .......................... A61K 9/68; A61K 7/16
[52] U.S. Cl. .......................................... 424/48; 424/49
[58] Field of Search .................................. 424/48–54, 424/131

[56] References Cited

U.S. PATENT DOCUMENTS

| | | | |
|---|---|---|---|
| 1,817,664 | 8/1931 | Badanes | 424/49 |
| 2,843,521 | 7/1958 | Entrekin | 424/49 |
| 2,894,876 | 7/1959 | Scanlan et al. | 424/48 |
| 3,728,446 | 4/1973 | Roberts | 424/49 |

*Primary Examiner*—Henry R. Jiles
*Assistant Examiner*—Cary Owens
*Attorney, Agent, or Firm*—Lawrence S. Levinson; Merle J. Smith; Burton Rodney

[57] ABSTRACT

A breath freshener composition is provided which may be in the form of a comestible, such as a pill, powder, tablet, pressed candy or mint, boiled candy, mouthwash, dental cream, chewing gum and the like, and which includes as its active ingredient calcium hydroxide alone or combinations of calcium hydroxide and magnesium hydroxide or combinations of magnesium hydroxide and/or calcium hydroxide with copper gluconate. In addition, a method is provided for inhibiting bad breath wherein calcium hydroxide alone or any of the above combinations is employed.

13 Claims, No Drawings

BREATH FRESHENER COMPOSITION AND METHOD

The present invention relates to a breath freshener composition which includes as its active ingredient calcium hydroxide or combinations of calcium hydroxide and/or magnesium hydroxide and/or copper gluconate and to a method for inhibiting bad breath employing such compositions.

Bad breath or mouth malodor is generally attributed to stale or putrified saliva. It has also been shown that mouth malodor is associated with sulfur compounds which are generated by decomposition of three amino acids in the saliva, namely, methionine, cystine and cysteine, to produce hydrogen sulfide, methyl mercaptan and dimethyl sulfide and sometimes dimethyl disulfide; for example see Tonzetich, "Direct Gas Chromatographic Analysis of Sulphur Compounds in Mouth Air in Man," Arch Oral Biol., Vol. 16, pp. 587–597, 1971; Tonzetich et al, "Evaluation of Volatile Odoriferous Components of Saliva," Arch Oral Biol., Vol. 9 pp. 39–45, 1964; and Tonzetich et al, "Odour Product by Human Salivary Fractions and Plaque," Arch Oral Biol., Vol. 14, pp. 815–827, 1969.

U.S. Pat. No. 2,926,121 to Hobbs et al discloses an antacid composition which contains a fully hydrated alumina gel as the primary ingredient and which may contain other antacids, namely, magnesium hydroxide, magnesium trisilicate or calcium carbonate.

British Patent Specification No. 294,299, U.S. Pat. Nos. 2,525,072 to Kearby, 1,630,763 to Raymer and Australian Patent Specification 131,394 disclose chewing gum compositions which include magnesium oxide or hydroxide or calcium carbonate.

U.S. Pat. Nos. 2,894,876 and 3,044,939 to Scanlan et al disclose oral deodorant candy tablets and chewing gum containing copper gluconate preferably in combination with a glyceride fat or oil.

U.S. Pat. Nos. 3,565,933 and 3,655,868 to Vagenius disclose an oral deodorant containing a water soluble reaction product of copper gluconate and glycine, the latter U.S. Pat. No. 3,655,868 also including ferrous gluconate.

It has now been found that bad breath due to mouth malodor is effectively inhibited by comestibles containing calcium hydroxide alone or combinations of calcium hydroxide with magnesium hydroxide, combinations of calcium hydroxide and copper gluconate, combinations of magnesium hydroxide and copper gluconate, and combinations of calcium hydroxide, magnesium hydroxide and copper gluconate.

In fact, it has been found that a combination of calcium hydroxide and magnesium hydroxide, and a combination of magnesium hydroxide and calcium gluconate are more effective in inhibiting bad breath than the additive effect of either component of each combination alone thereby indicating that such combinations are synergistic combinations. Furthermore, it has been found that the effectiveness of copper gluconate in inhibiting bad breath can be greatly increased by employing it in combinations containing calcium hydroxide.

It will be appreciated that the terms "calcium hydroxide" and "magnesium hydroxide" will also encompass calcium oxide and magnesium oxide, respectively.

The calcium hydroxide and the various combinations set out above may be employed in various comestibles such as pressed candies or mints, boiled candies or drops as well as in dental creams or powders, mouth washes, chewing gums and the like.

The calcium hydroxide, where employed alone without magnesium hydroxide or copper gluconate, will be present in an amount within the range of from about 0.05 to about 1%, and preferably from about 0.1 to about 0.7% by weight of the comestible (regardless of the type). Thus, for example, a unit dosage of candy (pressed or boiled), chewing gum, dental cream or mouth wash may contain from about 1 to about 10 mg, and preferably from about 2.5 to about 9.5 mg of calcium hydroxide. While amounts greater than 10 mg are effective, and may be employed, if desired, it has been found that amounts of calcium hydroxide greater than 10 mg may cause taste or flavor problems in a comestible.

Where the calcium hydroxide is employed in confections containing sugar prepared via wet techniques such as boiled candies, the calcium hydroxide may cause browning of the sugar. In such case, it is preferred to use amounts of calcium hydroxide of less than about 0.5% and preferably less than about 0.3% by weight of the confection. Alternatively, the calcium hydroxide may be employed in encapsulated form so as to prevent direct contact of wet sugar with the calcium hydroxide; in this case, the calcium hydroxide may be employed in amounts up to 1%.

Where the calcium hydroxide is employed in combination with magnesium hydroxide, the combined weight of this combination will be from about 0.05 to about 2%, and preferably from about 0.15 to about 1.5% by weight of the comestible. Thus, for example, each of the calcium hydroxide and magnesium hydroxide may be present in an amount within the range of from about 1 to about 10 mg, and preferably from about 1 to about 5 mg, so as to provide a weight ratio of calcium hydroxide:magnesium hydroxide within the range of from about 0.1:1 to about 10:1, and preferably from about 0.5:1 to about 2:1.

Where the calcium hydroxide is employed in combination with copper gluconate, the combined weight of this combination will be from about 0.05 to about 1%, and preferably from about 0.15 to about 0.6% by weight of the comestible with the copper gluconate alone being from about 0.005 to about 0.01% of the comestible. Thus, for example, the calcium hydroxide may be present in an amount within the range of from about 1 to about 10 mg, and preferably from about 1 to about 5 mg, while the copper gluconate may be present in an amount within the range of from about 0.01 to about 0.05 mg, and preferably from about 0.01 to about 0.04 mg so as to provide a weight ratio of copper gluconate:calcium hydroxide within the range of from about 0.05:1 to about 0.1:1, and preferably from about 0.06:1 to about 0.09:1.

Where the magnesium hydroxide is employed in combination with copper gluconate, the combined weight of this combination will be from about 0.05 to about 1%, and preferably from about 0.15 to about 0.6% by weight of the comestible with the copper gluconate alone being from about 0.005 to about 0.01% by weight of the comestible. Thus, for example, the magnesium hydroxide may be present in an amount within the range of from about 1 to about 10 mg, and preferably from about 1 to about 5 mg, while the copper gluconate may be present in an amount within the range of from about 0.01 to about 0.05 mg and preferably from about 0.01 to about 0.04 mg so as to provide a weight ratio of copper gluconate:magnesium hydroxide within the range of from about 0.05:1 to about 0.1:1, and preferably from about 0.06:1 to about 0.09:1.

Where the calcium hydroxide is employed in combination with both magnesium hydroxide and copper gluconate, the combined weight of the combination will be from about 0.05 to about 2%, and preferably from about 0.15 to about 1.6% by weight of the comestible. The copper gluconate will be present in amounts within the range of from about 0.005 to about 0.01%, and preferably from about 0.007 to about 0.009% by weight of the comestible while each of the calcium hydroxide and magnesium hydroxide will be present in amounts within the range of from about 0.05 to about 1%, and preferably from about 0.15 to about 1% by weight. Thus, for example, each of the calcium hydroxide and magnesium hydroxide may be present in an amount within the range of from about 1 to about 10 mg, and preferably from about 1 to about 5 mg, and the copper gluconate may be present in an amount within the range of from about 0.01 to about 0.05 mg, and preferably from about 0.01 to about 0.04 mg.

In an alternative embodiment of the present invention, magnesium hydroxide may be employed as a breath freshener in relatively small amounts in pressed or boiled candies within the range of from about 0.05 to about 0.6%, and preferably from about 0.1 to about 0.5% by weight of the candy. The fact that such small amounts of magnesium hydroxide are effective in inhibiting formation of malodors in the mouth is indeed surprising in view of the present use of about 1% by weight magnesium hydroxide in breath mints that have been marketed for several years.

In use, the comestible containing the calcium hydroxide and the various combinations set out above are particularly useful in inhibiting or preventing the onset of bad breath due to lack of saliva flow. Thus, for example, the comestible of the invention may be administered in the morning after a night's sleep or after a nap or at any time during the day when one's mouth is dry.

The effectiveness of the calcium hydroxide and the various combinations of the invention in inhibiting formation of malodorous sulfur compounds in saliva is shown by the following.

Procedure for Collection of Saliva and Sampling of Headspace

Saliva is collected (by stimulating with odorless and tasteless wax; Sun Oil Co.'s 1290 Y wax) in a wide mouth graduated tapered bottom test tube. The volume of saliva collected depends on the amount needed and varies from 15 to 25 ml. Three mls. aliquots are transferred into 7 drams vials which are sealed with Teflon-rubber lined screw caps to provide an air-tight seal. The sample is stored either at room temperature or at 98°–99° F. If an additive is required in a sample, the additive is weighed in the vial prior to introduction of the saliva sample. A Hamilton gas tight syringe with a Teflon coated plunger and a hypodermic needle are used to remove 10 ml aliquots of headspace for gas chromatographic sulfur analysis. This is achieved by means of a 3–4 mm hole in the plastic cap. The cap is then opened, the odor is evaluated, the Teflon-rubber liner is replaced with a new liner and the vial is recapped for further storage.

Prior to saliva collection, the subject's mouth air is sampled and analyzed for sulfur by gas chromatography. Ten ml of mouth air is withdrawn from the subject's mouth after breathing only through the nose with the mouth closed for one minute, then a clean polyethylene tube is attached to the Luer tip of the syringe, which is described above, and inserted quickly in the mouth, the subject is asked to stop breathing, and the sample (10 cc) is quickly collected from the oral cavity. The tube is quickly replaced with a hypodermic needle and the entire sample is injected on the gas chromatographic column directly.

Apparatus and Experimental Conditions

Instrument: Micro-Tek MT-220 gas chromatograph with solic state electrometers, and 750 V power supply, a flame photometric detector with 394 nm filter. The dual solid stage electrometer enables monitoring of the photomeric and flame ionization detectors output simultaneously. The recorder is Sargent's Model SRLG, at 1 mv span and 0.5 inch/min. chart speed.

The individual sulfur compounds are separated on a 24 ft × 1/8 in. Teflon column packed with 20% carbowax 20 M on 60–80 mesh chromosorb W (acid washed and DMCS treated). The analyses are performed at isothermal column temperature of 60° C. The temperature of the injection port is 150°–160° C and the temperature of the detector is 170°–180° C. The pressures and flow rates of the high purity gases are: $N_2$ carrier gas (40 psig) — 30 cc/min., $H_2$ (40 psig) – 180 cc. min., air (40 psig) — 45 cc/min., $O_2$ (40 psig) — 35 cc/min. At these parameters the following peaks and retention times are given:

| Peak | Retention Time |
| --- | --- |
| Air | 1.8 – 1.9 mins. |
| $H_2S$ | 2.2 – 2.4 mins. |
| $CH_3SH$ | 3.5 – 3.7 mins. |
| $(CH_3)_2S$ | 4.7 – 4.9 mins. |
| $SO_2$ | 6.6 – 6.8 mins. |
| $(CH_3S)_2$ | 28.6 – 28.9 mins. |

Calculations and Calibrations

The peak areas of the sulfur compounds are measured by the "height × width at ½ height" method. The total sulfur peak areas is obtained by summing individual peak areas after adjusting for attenuation scale.

Ethanol solutions containing both $(CH_3)_2S$, and $(CH_3S)_2$ (at concentrations ranging from 10. ppm of each to 100 ppm of each) are injected in amounts to give 1.2 ng to 120 ng total sulfur concentration per injection. The peak areas are measured and a log log graph is made of areas vs. concentration. Concentration of sulfur in the samples is estimated from the graph.

Correlation of the Odor of Putrified Saliva to sulfur Compounds a. After incubation of 1–2 hours at 98°–100° F, whole saliva samples shows distinct putrification and appreciable increase of concentration of sulfur in the headspace. In fresh saliva, the concentration of sulfur in the headspace ranges from 0 to 0.5 ng and in samples incubated for 1 ½ hours at 98° F it ranges from 3.0 to 12.0 ng.

b. After incubation of saliva samples at room temperature the concentration of sulfur increases gradually during the first 3 hours, but dramatic increase in both sulfur concentration and putrefaction is noted after 4 hours.

c. The odor of putrefied saliva is simulated in water by adding 1 ul of air saturated with methyl mercaptan to 5 ml of distilled water.

d. In addition to the three sulfur compounds ($H_2S$, $(CH_3)_2S$, and $CH_3SH$) which are correlated with mouth malodor, another sulfur compound, dimethyl disulfide $(CH_3S)_2$, is noted in headspace of all putrefied saliva samples which were stored for 24 hours or longer at room temperature and for 3 hours or longer at 98° F.

Prolonged storage of saliva at 98° F (i.e. 24 hours or longer) does not produce an appreciable increase in sulfur concentration, and a drop in the strength of the putrefied odor is noted. At room temperature storage the concentration of sulfur in the headspace and the putrefied odor continually increase. Room temperature storage is used for most of the samples studies to date, since it provides for a better comparison between the samples in the long range.

In addition to magnesium hydroxide, calcium hydroxide and copper gluconate are tested as additives in saliva samples and found to effectively retard putrefaction of saliva as seen from the low sulfur concentrations in the headspace and the low ratings on the unpleasant odor scale as can be seen from the following Table.

Table I

Headspace Analyses and Odor Evaluation of Whole Saliva Stored at Room Temperature and Affect of $Ca(OH)_2$, $Mg(OH)_2$, Cu Gluconate and Combinations Thereof

| Run No. | Additive Amount | Age of Sample Hrs & min. | Total Sulfur Concentraton in 10cc Headspace (nanograms, ng) | Odor Evaluation (Magnitude of Unpleasant Odor- 0 to 10 0=no unpleasant odor 10=very putrified odor) |
|---|---|---|---|---|
| Control A | — | 2 hrs 35 min | 1.30 | 6 |
| Control B | Cu gluconate (0.033 mg) | 2 hrs 50 min | 1.68 | 2 |
| 1 | $Ca(OH)_2$ (10 mg) | 3 hrs 24 min | 0.92 | 1 |
| 2 | Spray dried (SD) $Mg(OH)_2$ (15 mg) | 3 hrs 10 min | 1.32 | 2 |
| 3 | $Ca(OH)_2$ (10 mg) + Cu gluconate (0.033 mg) | 3 hrs 54 min | 0.67 | 1 |
| 4 | SD $Mg(OH)_2$ (15 mg) + Cu gluconate (0.033 mg) | 3 hrs 42 min | 1.00 | 3 |
| 5 | $Ca(OH)_2$ (5 mg) | 4 hrs 10 min | 0.70 | 2 |
| Control C | — | 4 hrs 31 min | 2.60 | 8 |
| Control D | — | 18 hrs 32 min | 7.30 | 10 |
| 6 | $Ca(OH)_2$ (8.9 mg) | 19 hrs 50 min | 0.22 | 0 |
| 7 | SD $Mg(OH)_2$ (9.7 mg) | 19 hrs 21 min | 2.3 | 1 |
| Control E | Cu gluconate | 19 hrs 5 min | 5.50 | 2 |
| 8 | $Ca(OH)_2$ (8.6 mg) + Cu gluconate (0.07 mg) | 20 hrs 8 min | 0.40 | 0 |
| 9 | SD $Mg(OH)_2$ (9.4 mg) + Cu gluconate (0.07 mg) | 19 hrs 36 mn | 0.83 | 0 |
| Control F | — | 44 hrs 35 min | 470 | 10 |
| Control G | Cu gluconate (0.07 mg) | 46 hrs 17 min | 2.9 | 2 |
| 10 | $Ca(OH)_2$ (8.9 mg) | 45 hrs 57 min | 0 | 0 |
| 11 | SD $Mg(OH)_2$ (9.7 mg) | 44 hrs 52 min | 2.2 | 1 |
| 12 | $Ca(OH)_2$ (8.6 mg) + Cu gluconate (0.07 mg) | 46 hrs 6 min | 0 | 0 |
| 13 | SD $Mg(OH)_2$ (9.4 mg) + Cu gluconate (0.07 mg) | 45 hrs 45 min | 0.5 | 0 |
| Control H | — | 52 hrs 11 min | 330 | 10 |
| Control I | Cu gluconate (0.033 mg) | 53 hrs 17 min | 380 | 10 |
| 14 | $Ca(OH)_2$ (10 mg) | 52 hrs 57 min | 0.72 | 3 |
| 15 | $Ca(OH)_2$ (5 mg) | 54 hrs 9 min | 0.50 | 3 |
| 16 | SD $Mg(OH)_2$ (15 mg) | 52 hrs 45 min | 1.10 | 3 |
| 17 | $Ca(OH)_2$ (10 mg) + Cu gluconate (0.033 mg) | 54 hrs 0 min | 0.89 | 3 |

Table I-continued

Headspace Analyses and Odor Evaluation of Whole Saliva Stored at Room Temperature and Affect of $Ca(OH)_2$, $Mg(OH)_2$, Cu Gluconate and Combinations Thereof

| Run No. | Additive Amount | Age of Sample Hrs & min. | Total Sulfur Concentraton in 10cc Headspace (nanograms, ng) | Odor Evaluation (Magnitude of Unpleasant Odor- 0 to 10; 0=no unpleasant odor 10=very putrified odor) |
|---|---|---|---|---|
| 18 | SD $Mg(OH)_2$ (15 mg) + Cu gluconate (0.033 mg) | 53 hrs 49 min | 0.54 | 3 |
| Control J | — | 68 hrs 0 min | 120 | 10 |
| 19 | $Ca(OH)_2$ (2.4 mg) | 68 hrs 13 min | 2.6 | 1 |
| 20 | $Ca(OH)_2$ (3.4 mg) | 68 hrs 21 min | 0.61 | 1 |
| 21 | $Mg(OH)_2$ (9.7 mg) | 68 hrs 33 min | 0.45 | 1 |
| 22 | SD $Mg(OH)_2$ (13.2 mg) | 68 hrs 42 min | 0.52 | 1 |

SD $Mg(OH)_2$ is spray dried magnesium hydroxide on gum arabic. The powder used contains 75% magnesium hydroxide.
ng = nanogram or one billionth of a gram Table II Headspace Analyses And Odor Evaluation of Whole Saliva Samples Stored at 98°F. and Affect of $Ca(OH)_2$ and $Mg(OH)_2$ Thereon

| Run No. | Additive Amount | Age of Sample Hrs & min | Total Sulfur Concentration in 10cc Headspace (nanograms, ng) | Odor Evaluation (Magnitude of Unpleasant Odor- 0=no unpleasant odor 10=very putrified odor) |
|---|---|---|---|---|
| Control K | — | 30 min | 1.52 | 4 |
| 23 | $Ca(OH)_2$ (9.4 mg) | 37 min | 0.47 | 1 |
| 24 | SD $Mg(OH)_2$ (11.5 mg) | 45 min | 1.52 | 1 |
| Control L | — | 2 hrs 2 min | 3.3 | 10 |
| 25 | $Ca(OH)_2$ (9.4 mg) | 2 hrs 18 min | 0.39 | 1 |
| 26 | SD $Mg(OH)_2$ (11.5 mg) | 2 hrs 11 min | 1.9 | 1 |
| Control M | — | 20 hrs 25 min | 4.9 | 4 |
| 27 | $Ca(OH)_2$ (9.4 mg) | 21 hrs 8 min | 0 | 0 |
| 28 | SD $Mg(OH)_2$ (11.5 mg) | 20 hrs 45 min | 2.0 | 1 |

SD $Mg(OH)_2$ is spray dried magnesium hydroxide on gum arabic. The powder used contains 75% magnesium hydroxide.
ng=nanogram or one billionth of a gram Table III Headspace Analysis and Odor Evaluation of Saliva Centrifugate Stored at Room Temperature and Affect of $Ca(OH)_2$ and $Mg(OH)_2$ and Combinations thereof thereon

| Run No. | Additive Amount | Age of Sample Hrs & Min | Total Sulfur Concentration in 10cc Headspace (nanograms mg) | Odor Evaluation (magnitude of Unpleasant Odor 0=no unpleasant odor 10=very putrified odor) |
|---|---|---|---|---|
| Control N | — | 68 hrs 40 min | 12.0 | 10 |
| 29 | $Ca(OH)_2$ (1.7 mg) | 68 hrs 51 min | 0.70 | 1 |
| 30 | $Mg(OH)_2$ (2.6 mg) | 69 hrs 2 min | 1.80 | 2 |
| 31 | $Ca(OH)_2$ (1.8 mg) + $Mg(OH)_2$ (2.4 mg) | 69 hrs 19 min | 0.42 | ½ |
| Control O | — | 10 days | — | 10 |
| 32 | $Ca(OH)_2$ (1.7 mg) | 10 days | — | 3½ |
| 33 | $Mg(OH)_2$ (2.6 mg) | 10 days | — | 3½ |
| 34 | $Ca(OH)_2$ (1.8 mg) + $Mg(OH)_2$ (2.4 mg) | 10 days | — | 2 |

Table III-continued
Headspace Analysis and Odor Evaluation of
Saliva Centrifugate Stored at Room Temperature
and Affect of Ca(OH)₂ and Mg(OH)₂
and Combinations thereof thereon

| Run No. | Additive Amount | Age of Sample Hrs & Min | Total Sulfur Concentration in 10cc Headspace (nanograms mg) | Odor Evaluation (magnitude of Unpleasant Odor 0=no unpleasant odor 10=very putrified odor) |
|---|---|---|---|---|
| Control P | — | 14 days | — | 10 |
| 35 | Ca(OH)₂ (1.7 mg) | 14 days | — | 7 |
| 36 | Mg(OH)₂ (2.6 mg) | 14 days | — | 4 |
| 37 | Ca(OH)₂ (1.8 mg) + Mg(OH)₂ (2.4 mg) | 14 days | — | 2 |

SD Mg(OH)₂ is spray dried magnesium hydroxide on gum arabic. The powder used contains 75% magnesium hydroxide.
ng=nanogram or one billionth of a gram The results in the above Table clearly show that calcium hydroxide alone; combinations of calcium hydroxide and magnesium hydroxide; combinations of calcium hydroxide and copper gluconate; combinations of magnesium hydroxide and copper gluconate; and magnesium hydroxide alone (at very low levels) are effective in inhibiting formation of sulfur compounds which contribute to mouth malodor.

The following examples illustrate the present invention without, however, limiting the same thereto. Each of the following compositions are effective in inhibiting onset of bad breath.

EXAMPLE 1

A pressed mint is prepared from the following formulation:

| Mint granulation | 98.1% |
|---|---|
| Ca(OH)₂ | 0.5% |
| Calcium stearate | 1.0% |
| Flavoring oil | 0.4% |

EXAMPLE 2

A boiled drop is prepared from the following formulation:

| Sugar | 74.3% |
|---|---|
| Corn Syrup 43° Be | 25.0% |
| Ca(OH)₂ | 0.2% |
| Flavor | 0.5% |

EXAMPLE 3

A mouth wash is prepared from the following formulation:

| Ca(OH)₂ | 5.00 gm |
|---|---|
| Sodium chloride | 8.00 gm |
| Sodium bicarbonate | 2.50 gm |
| Glycerin | 420.00 ml |
| Alcohol | 300.00 ml |
| Menthol | 0.24 gm |
| Thymol | 0.24 gm |
| Methyl salicylate | 0.70 ml |
| Cinnamon oil | 0.50 ml |
| Eucalyptus oil | 1.30 ml |
| Cudbear tincture | 16.00 ml |
| Krameria tincture | 8.00 ml |
| Purified talc | 20.00 gm |
| Purified water | sufficient to make 1,000.00 ml |

EXAMPLE 4

A dental cream is prepared having the following composition:

| Precipitated calcium carbonate | 44.6% |
|---|---|
| Ca(OH)₂ | 0.4% |
| Sodium lauryl sulfate | 1.5% |
| Glycerin | 15.0% |
| Sorbitol (70% solution) | 15.0% |
| Na saccharin | 0.1% |
| Methyl p-hydroxy benzoate | 0.1% |
| Na alginate 21 | 1.5% |
| Flavor | 1.1% |
| Purified water | 20.7% |

EXAMPLE 5

A chewing gum is prepared from the following formulation:

| | Parts by Weight |
|---|---|
| Gum base | 20 |
| Sorbitol | 10 |
| Ca(OH)₂ | 0.5 |
| Lecithin (softener) | 0.5 |
| Na Saccharin | 0.1 |
| Ca carbonate (filler) | 10 |
| Peppermint flavor oil | 0.5 |

EXAMPLE 6

A pressed mint is prepared from the following formulation:

| Mint granulation | 97.6% |
|---|---|
| Ca(OH)₂ | 0.5% |
| Mg(OH)₂ | 0.5% |
| Calcium stearate | 1.0% |
| Flavoring oil | 0.4% |

EXAMPLE 7

A boiled drop is prepared from the following formulation:

| Sugar | 73.5% |
|---|---|

|  | |
|---|---|
| Corn Syrup 43° Be | 25.0% |
| Ca(OH)$_2$ | 0.2% |
| Mg(OH)$_2$ | 0.8% |
| Flavor | 0.5% |

EXAMPLE 8

A mouth wash is prepared from the following formulation:

|  | |
|---|---|
| Magnesium hydroxide | 2.50 gm |
| Calcium hydroxide | 2.50 gm |
| Sodium chloride | 8.00 gm |
| Sodium bicarbonate | 2.50 gm |
| Glycerin | 420.00 ml |
| Alcohol | 300.00 ml |
| Menthol | 0.24 gm |
| Thymol | 0.24 gm |
| Methyl salicylate | 0.70 ml |
| Cinnamon oil | 0.50 ml |
| Eucalyptus oil | 1.30 ml |
| Cudbear tincture | 16.00 ml |
| Krameria tincture | 8.00 ml |
| Purified talc | 20.00 gm |
| Purified water | sufficient to make 1,000.00 ml. |

EXAMPLE 9

A dental cream is prepared having the following composition:

|  | |
|---|---|
| Precipitated calcium carbonate | 44.0% |
| Ca(OH)$_2$ | 0.6% |
| Mg(OH)$_2$ | 0.4% |
| Sodium lauryl sulfate | 1.5% |
| Glycerin | 15.0% |
| Sorbitol (70% solution) | 15.0% |
| Ca Saccharin (soluble) | 0.1% |
| Methyl p-hydroxy benzoate | 0.1% |
| Na alginate 21 | 1.5% |
| Flavor | 1.1% |
| Purified water | 20.7% |

EXAMPLE 10

A chewing gum is prepared from the following formulation:

|  | Parts by Weight |
|---|---|
| Gum Base | 20 |
| Ca(OH)$_2$ | 0.2 |
| Mg(OH)$_2$ | 0.3 |
| Sucrose | 50 |
| Sorbitol | 10 |
| Corn Syrup | 19 |

EXAMPLE 11

A pressed mint is prepared from the following formulation:

|  | Parts by Weight |
|---|---|
| Mint granulation | 97.6 |
| Ca(OH)$_2$ | 0.5 |
| Cu gluconate | 0.03 |
| Calcium stearate | 1.0 |
| Flavoring oil | 0.4 |

EXAMPLE 12

A boiled drop is prepared from the following formulation:

|  | Parts by Weight |
|---|---|
| Sugar | 73.5 |
| Corn Syrup 43° Be | 25.0 |
| Ca(OH)$_2$ | 0.2 |
| Copper gluconate | 0.04 |
| Flavor | 0.5 |

EXAMPLE 13

A mouth wash is prepared from the following formulation:

|  | |
|---|---|
| Calcium hydroxide | 5.00 gm |
| Copper gluconate | 0.3 gm |
| Sodium chloride | 8.00 gm |
| Sodium bicarbonate | 2.50 gm |
| Glycerin | 420.00 ml |
| Alcohol | 300.00 ml |
| Menthol | 0.24 gm |
| Thymol | 0.24 gm |
| Methyl salicylate | 0.70 ml |
| Cinnamon oil | 0.50 ml |
| Eucalyptus oil | 1.30 ml |
| Cudbear tincture | 16.00 ml |
| Krameria tincture | 8.00 ml |
| Purified talc | 20.00 gm |
| Purified water | sufficient to make 1,000.00 ml. |

EXAMPLE 14

A dental cream is prepared having the following composition:

|  | Parts by Weight |
|---|---|
| Precipitated calcium carbonate | 44.0 |
| Ca(OH)$_2$ | 0.6 |
| Copper gluconate | 0.03 |
| Sodium lauryl sulfate | 1.5 |
| Glycerin | 15.0 |
| Sorbitol (70%) solution | 15.0 |
| Na Saccharin (soluble) | 0.1 |
| Methyl p-hydroxy benzoate | 0.1 |
| Na alginate 21 | 1.5 |
| Flavor | 1.1 |
| Purified water | 20.7 |

EXAMPLE 15

A chewing gum is prepared from the following formulation:

|  | Parts by Weight |
|---|---|
| Gum base | 20 |
| Ca(OH)$_2$ | 0.2 |
| Cu gluconate | 0.03 |
| Sucrose | 50 |
| Sorbitol | 10 |
| Corn Syrup | 19 |

EXAMPLE 16

A pressed mint is prepared from the following formulation:

|  | |
|---|---|
| Mint granulation | 98.1% |
| Mg(OH)$_2$ | 0.5% |
| Calcium stearate | 1.0% |
| Flavoring oil | 0.4% |

EXAMPLE 17

A boiled drop is prepared from the following formulation:

|  | Parts by Weight |
|---|---|
| Sugar | 73.0 |
| Corn Syrup 43° Be | 25.0 |
| $Ca(OH)_2$ | 0.2 |
| $Mg(OH)_2$ | 0.6 |
| Cu gluconate | 0.03 |
| Flavor | 0.5 |

EXAMPLE 18

A mouth wash is prepared from the following formulation:

| Magnesium hydroxide | 5.00 gm |
|---|---|
| Sodium chloride | 8.00 gm |
| Sodium bicarbonate | 2.50 gm |
| Glycerin | 420.00 ml |
| Alchohol | 300.00 ml |
| Menthol | 0.24 gm |
| Thymol | 0.24 gm |
| Methyl salicylate | 0.70 ml |
| Cinnamon oil | 0.50 ml |
| Eucalyptus oil | 1.30 ml |
| Cudbear tincture | 16.00 ml |
| Krameria tincture | 8.00 ml |
| Purified talc | 20.00 gm |
| Purified water | sufficient to make 1,000.00 ml |

EXAMPLE 19

A dental cream is prepared having the following composition:

|  | Parts by Weight |
|---|---|
| Precipitated calcium carbonate | 44.0 |
| $Ca(OH)_2$ | 0.6 |
| $Mg(OH)_2$ | 0.3 |
| Cu gluconate | 0.03 |
| Sodium lauryl sulfate | 1.5 |
| Glycerin | 15.0 |
| Sorbitol (70% solution) | 15.0 |
| Saccharin (soluble) | 0.1 |
| Methyl p-hydroxy benzoate | 0.1 |
| Na alginate 21 | 1.5 |
| Flavor | 1.1 |
| Purified water | 20.7 |

What is claimed is:

1. A breath freshener composition consisting essentially of calcium hydroxide dispersed in a non-toxic carrier.
2. The breath freshener composition as defined in claim 1 wherein said calcium hydroxide is present in an amount within the range of from about 0.05 to about 1% by weight.
3. The breath freshener composition as defined in claim 1 in the form of a comestible.
4. The breath freshener composition as defined in claim 3 wherein the comestible is a candy or chewing gum.
5. The breath freshener composition as defined in claim 3 wherein the comestible is a dental cream or mouth wash.
6. The breath freshener composition as defined in claim 1 further including magnesium hydroxide.
7. The breath freshener composition as defined in claim 6 wherein the calcium hydroxide is present in an amount within the range of from about 0.025 to about 1% by weight and the magnesium hydroxide is present in an amount within the range of from about 0.025 to about 1% by weight
8. The breath freshener composition as defined in claim 1 further including copper gluconate.
9. The breath freshener composition as defined in claim 8 wherein the calcium hydroxide is present in an amount within the range of from about 0.04 to about 0.99% by weight and the copper gluconate is present in an amount within the range of from about 0.005 to about 0.01% by weight.
10. The breath freshener composition as defined in claim 8 further including magnesium hydroxide in an amount within the range of from about 0.04 to about 0.99% by weight.
11. A method for inhibiting onset of bad breath which comprises chewing, applying to the teeth or rinsing in the mouth a composition as defined in claim 1.
12. A method for inhibiting onset of bad breath which comprises chewing, applying to the teeth or rinsing in the mouth a composition as defined in claim 6.
13. A method for inhibiting onset of bad breath which comprises chewing, applying to the teeth or rinsing in the mouth a composition as defined in claim 8.

* * * * *